United States Patent
Zhou et al.

(10) Patent No.: US 10,954,367 B2
(45) Date of Patent: Mar. 23, 2021

(54) REINFORCED THERMOPLASTIC POLYOLEFIN ELASTOMER FILM

(71) Applicant: KIMBERLY-CLARK WORLDWIDE, INC., Neenah, WI (US)

(72) Inventors: Peiguang Zhou, Appleton, WI (US); WanDuk Lee, Appleton, WI (US); Davis Dang H. Nhan, Menasha, WI (US); Vasily A. Topolkaraev, Appleton, WI (US); Michael G. Shlepr, Greenville, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 54 days.

(21) Appl. No.: 16/320,736

(22) PCT Filed: Aug. 11, 2017

(86) PCT No.: PCT/US2017/046419
§ 371 (c)(1),
(2) Date: Jan. 25, 2019

(87) PCT Pub. No.: WO2018/031847
PCT Pub. Date: Feb. 15, 2018

(65) Prior Publication Data
US 2019/0153205 A1 May 23, 2019

Related U.S. Application Data

(60) Provisional application No. 62/373,392, filed on Aug. 11, 2016.

(51) Int. Cl.
*C08L 23/12* (2006.01)
*C08J 5/18* (2006.01)
(Continued)

(52) U.S. Cl.
CPC .............. *C08L 23/12* (2013.01); *A61L 15/24* (2013.01); *B65D 65/38* (2013.01); *C08J 5/18* (2013.01);
(Continued)

(58) Field of Classification Search
CPC ...................................................... C08L 23/12
See application file for complete search history.

(56) References Cited

U.S. PATENT DOCUMENTS

| 5,043,205 A | 8/1991 | Perazzo et al. |
| 7,160,949 B2 | 1/2007 | Ota et al. |

(Continued)

FOREIGN PATENT DOCUMENTS

| RU | 2418821 C2 | 5/2011 |
| WO | 2013083999 A2 | 6/2013 |

(Continued)

*Primary Examiner* — Mark S Kaucher
(74) *Attorney, Agent, or Firm* — Kimberly-Clark Worldwide, Inc.

(57) ABSTRACT

A thermoplastic polyolefin elastomer film includes a continuous phase that includes a thermoplastic polyolefin elastomer and a nanoinclusion additive dispersed within the continuous phase in the form of discrete domains, wherein each discrete domain is elongated with a long axis, wherein the axes are aligned in the machine direction (MD) when the film is relaxed, and wherein the axes are aligned in the cross direction (CD) when the film is stretched in the CD. Also, an article includes the thermoplastic polyolefin elastomer film.

20 Claims, 4 Drawing Sheets

(51) Int. Cl.
*C08L 23/14* (2006.01)
*A61L 15/24* (2006.01)
*B65D 65/38* (2006.01)

(52) U.S. Cl.
CPC ........... *C08L 23/14* (2013.01); *C08J 2323/02* (2013.01); *C08J 2323/12* (2013.01); *C08J 2323/14* (2013.01); *C08J 2423/08* (2013.01); *C08J 2467/04* (2013.01); *C08L 2203/16* (2013.01); *C08L 2205/025* (2013.01); *C08L 2205/03* (2013.01); *C08L 2205/08* (2013.01); *C08L 2207/02* (2013.01); *C08L 2207/04* (2013.01)

(56) References Cited

U.S. PATENT DOCUMENTS

| | | | |
|---|---|---|---|
| 7,179,952 B2 | 2/2007 | Vukos et al. | |
| 7,776,020 B2 | 8/2010 | Kaufman et al. | |
| 8,246,878 B2 | 8/2012 | Sun et al. | |
| 8,568,636 B2 | 10/2013 | Jeon et al. | |
| 8,603,281 B2 | 12/2013 | Welch et al. | |
| 8,679,992 B2 | 3/2014 | Austin et al. | |
| 8,889,945 B2 | 11/2014 | Wang et al. | |
| 9,163,141 B2 | 10/2015 | Becraft et al. | |
| 2011/0177735 A1 | 7/2011 | Tasi et al. | |
| 2011/0240027 A1* | 10/2011 | Billingsley | D04H 1/413 128/205.12 |
| 2012/0040582 A1 | 2/2012 | Topolkaraev et al. | |
| 2013/0210308 A1 | 8/2013 | McEneany et al. | |
| 2013/0210949 A1 | 8/2013 | Scholl et al. | |
| 2014/0072743 A1 | 3/2014 | Stephenne et al. | |
| 2014/0272356 A1 | 9/2014 | He et al. | |
| 2015/0354109 A1 | 12/2015 | Ashraf | |
| 2016/0122484 A1 | 5/2016 | Topolkaraev et al. | |
| 2016/0177044 A1 | 6/2016 | Topolkaraev et al. | |
| 2016/0185929 A1 | 6/2016 | Topolkaraev et al. | |

FOREIGN PATENT DOCUMENTS

| | | | |
|---|---|---|---|
| WO | 13118023 A1 | 8/2013 | |
| WO | 14199270 A1 | 12/2014 | |
| WO | WO-2014199268 A1 * | 12/2014 | ........... B29C 55/005 |

* cited by examiner

REINFORCED THERMOPLASTIC POLYOLEFIN ELASTOMER FILM

BACKGROUND

Articles such as packages and absorbent articles can be constructed from a generally liquid-permeable layer, a generally liquid-impermeable layer, or a combination of these. Polyolefin films are often used in the construction of such layers of the article. For example, the components of many absorbent articles can include a polyethylene film. Because of the dynamic nature of the use of such products, it is desirable to use materials that exhibit stretchability and flexibility while maintaining strength and sealing properties. While attempts have been made to increase the elasticity of materials, these attempts have often led to costly and ineffective materials. As such, a need currently exists for films that can have increased elasticity without sacrificing performance or favorable properties when used in an article.

SUMMARY

In accordance with one aspect of the present disclosure, a film formed from a thermoplastic polyolefin elastomer composition that contains a continuous phase that includes a polyolefin elastomer matrix and a nanoinclusion additive dispersed within the continuous phase in the form of discrete domains. An inclusion network is defined in the composition that includes a plurality of nanoinclusions having an average cross-sectional dimension of about 800 nanometers or less. Each discrete domain is elongated with a long axis, wherein the axes are aligned in the machine direction (MD) when the film is relaxed, and wherein the axes are aligned in the cross direction (CD) when the film is stretched in the CD.

The present disclosure describes a thermoplastic polyolefin elastomer film including a continuous phase that includes a thermoplastic polyolefin elastomer and a nanoinclusion additive dispersed within the continuous phase in the form of discrete domains, wherein each discrete domain is elongated with a long axis, wherein the axes are aligned in the machine direction (MD) when the film is relaxed, and wherein the axes are aligned in the cross direction (CD) when the film is stretched in the CD.

The present disclosure also describes an article including a polyolefinic elastomeric film including a continuous phase that includes a thermoplastic polyolefin elastomer and a nanoinclusion additive dispersed within the continuous phase in the form of discrete domains, wherein each discrete domain is elongated with a long axis, wherein the axes are aligned in the machine direction (MD) when the film is relaxed, and wherein the axes are aligned in the cross direction (CD) when the film is stretched in the CD.

Other features and aspects of the present disclosure are discussed in greater detail below.

BRIEF DESCRIPTION OF THE DRAWINGS

A full and enabling disclosure of the present disclosure, including the best mode thereof, directed to one of ordinary skill in the art, is set forth more particularly in the remainder of the specification, which makes reference to the appended figures in which.

DETAILED DESCRIPTION

Figure 1:
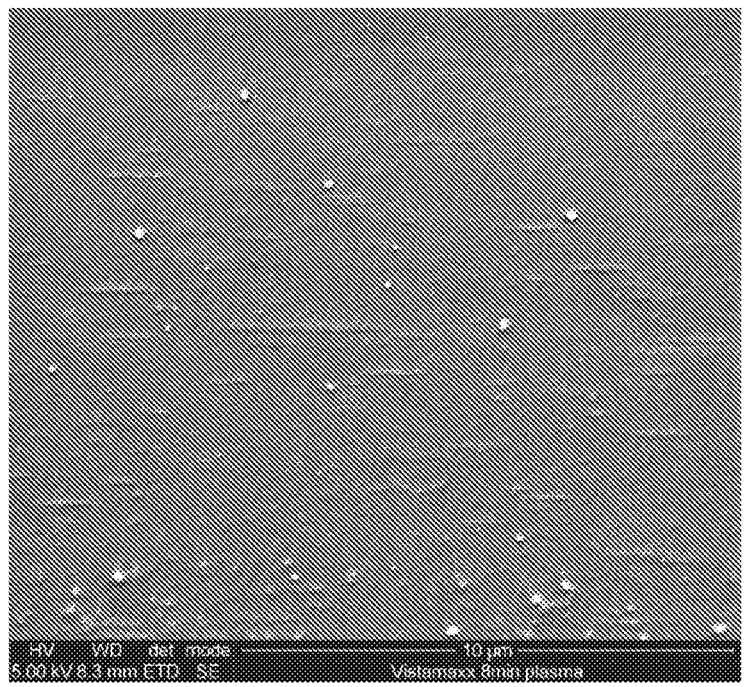
FIG. 1 is a scanning electron microscope (SEM) microphotograph of a surface of the film of comparison Sample 1 of 100% polyolefin-based elastic in the machine direction (MD)
Figure 2:
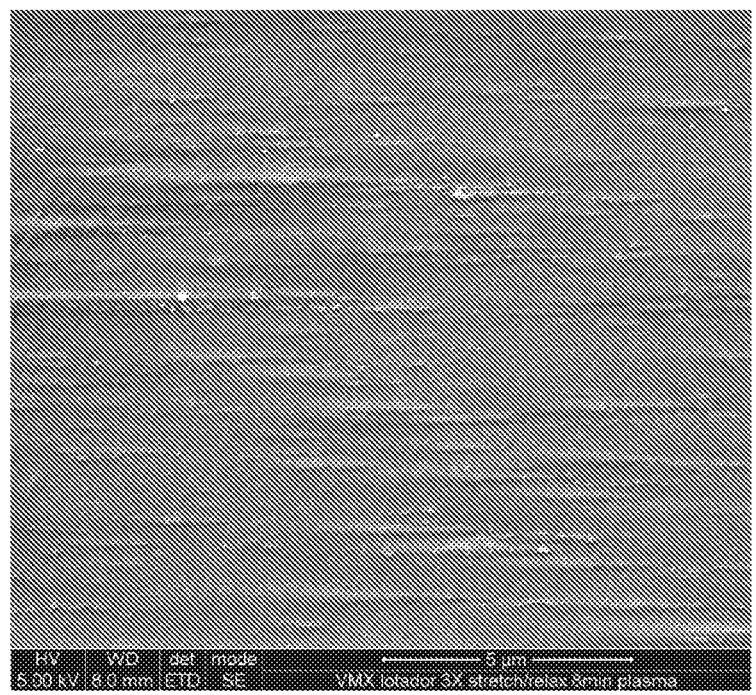
FIG. 2 is an SEM microphotograph of a surface of the film of experimental Sample 2 of 92.5% polyolefin-based elastic/7.5% polyolefin-based epoxy resin in the MD.
Figure 3:
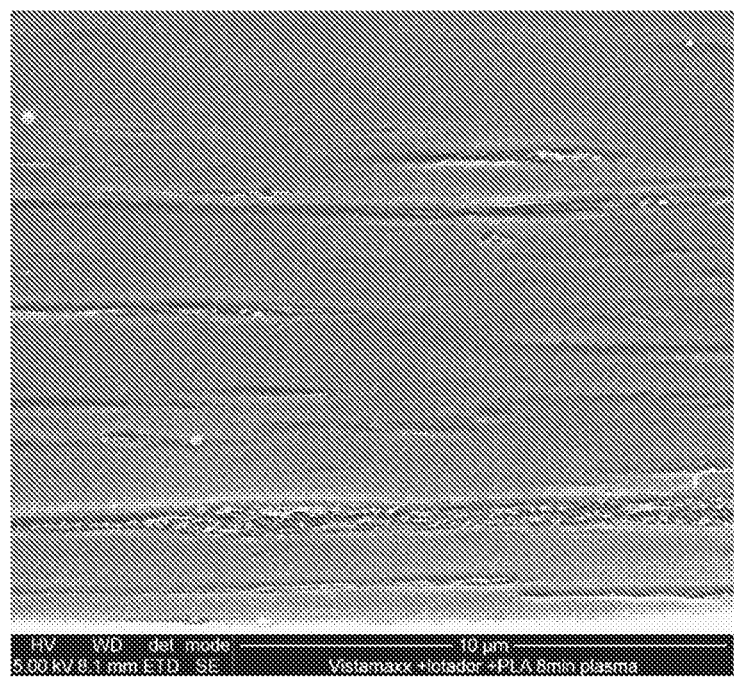
FIG. 3 is an SEM microphotograph of a surface of the film of experimental Sample 3 of 90% polyolefin-based elastic/5% polyolefin-based epoxy resin/5% polylactic acid in the MD.
Figure 4:
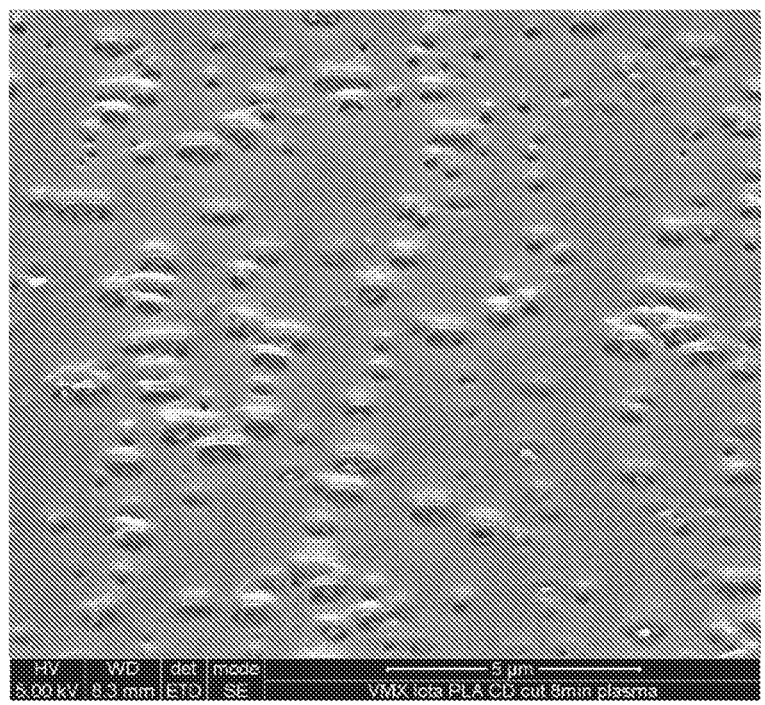
FIG. 4 is an SEM microphotograph of a surface of the film of experimental Sample 3 of 90% polyolefin-based elastic/5% polyolefin-based epoxy resin/5% polylactic acid in the CD.
Figure 5:
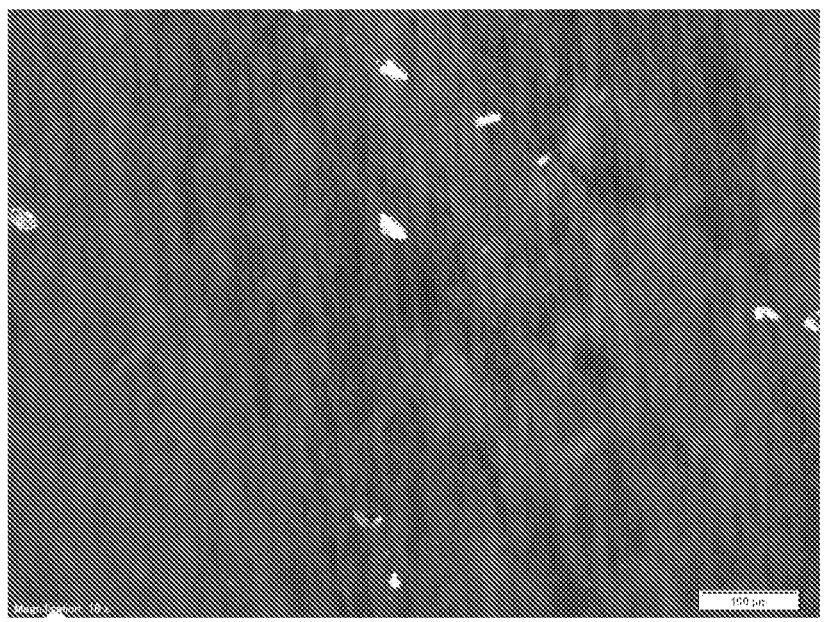
FIG. 5 is an SEM microphotograph of a surface of the film of 0% stretching in the CD, where micro-domains align in the MD.

Reference now will be made in detail to various aspects of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one aspect, can be used on another aspect to yield a still further aspect. Thus, it is intended that the present disclosure covers such modifications and variations as come within the scope of the appended claims and their equivalents.

As used herein, the terms "polymer" and "polymeric" generally include but are not limited to, homopolymers, copolymers, such as for example, block, graft, random, and alternating copolymers, terpolymers, etc. and blends and modifications thereof. Furthermore, unless otherwise specifically limited, the term "polymer" includes all possible spatial configurations of the molecule. These configurations include, but are not limited to isotactic, syndiotactic, and random symmetries.

As used herein, the terms "machine direction" or MD refers to the direction along the length of a fabric in the direction in which it is produced. The terms "cross machine direction," "cross direction," "cross directional," or CD refers to the direction across the width of the fabric, i.e., a direction generally perpendicular to the MD.

As used herein, the term "elastomeric" and "elasticity" shall be interchangeable with the term "elastic" and refers to sheet material that, upon application of a stretching force, is stretchable in at least one direction (such as the CD), and that upon release of the stretching force contracts/returns to approximately its original dimension. An elastomeric material can be elongated by at least 25 percent of its relaxed length and will recover, upon release of the applied force, at least 10 percent of its elongation. It is generally desirable that the elastomeric material or composite be capable of being elongated by at least 100 percent, more desirably by at least 300 percent, and even more desirably by at least 400 percent, of its relaxed length and recover, upon release of an applied force, at least 50 percent of its elongation.

As used herein, the term "elastomer" refers to a polymer that is elastomeric when in a solid state.

As used herein, the term "thermoplastic" refers to a polymer that is capable of being extruded at high temperatures when in a molten state. In the present disclosure, a thermoplastic polymer is a polyolefin elastomer.

As used herein, the term "inclusion" generally refers to a material that is capable of being dispersed within the polymer matrix in the form of discrete domains.

As used herein, the term "aspect ratio" of an inclusion means the ratio of the axial dimension to a dimension orthogonal to the axial dimension of that inclusion.

As used herein, the term "set" refers to retained elongation in a material sample following the elongation and recovery, i.e., after the material has been stretched and allowed to relax by removing the initially-applied tension during a cycle test.

As used herein, the term "permanent set" is the measure of the percent (%) amount elongation at which stress becomes zero after removing the initially-applied tension, as shown in a stress-% elongation plot. A perfect elastic material such as a spring would have a zero permanent set because the retractive curve will pass through the origin. As used herein, permanent set is measured after 150% elongation of the material. For example, a material sample with an initial gauge length of 1 inch that is stretched to 150% elongation and relaxes back to a length of about 1.2 inches has a permanent set, as defined herein, of 20%.

Generally speaking, the present disclosure is directed to thermoplastic polyolefin elastomer compositions used in films or other articles, wherein articles made using the composition have increased tensile strength and elasticity, particularly in the cross-machine direction. The composition can be used in films, laminates, packaging, personal care articles, and in any other suitable application. In one exemplary application, the composition can be used in an absorbent article that is capable of absorbing water or other fluids. Examples of some absorbent articles include, but are not limited to, personal care absorbent articles, such as diapers, training pants, absorbent underpants, adult incontinence articles, feminine hygiene products (e.g., sanitary napkins), swim wear, baby wipes, mitt wipes, and so forth; medical absorbent articles, such as garments, fenestration materials, underpads, bandages, absorbent drapes, and medical wipes; food service wipers; clothing articles; and so forth.

Stronger CD elastics with good percent set properties are important for product applications such as materials for diaper ears or side panels for pants.

The thermoplastic polyolefin elastomer composition contains a continuous phase that includes a polyolefin elastomer matrix, and also contains a nanoinclusion additive that is at least partially incompatible with the polyolefin elastomer matrix so that it becomes dispersed within the continuous phase as discrete nano-scale phase domains.

A dispersed reinforcing elongated inclusion structure can be created in an elastomeric matrix. Inclusion of polyolefin-based epoxy resin and/or polylactic acid (PLA) nano- and micro-domains in a polyolefin elastic matrix enhances tensile strength and maintains good elastic properties in the cross-machine direction (CD). The materials described herein provide a technological breakthrough in developing strong CD-stretchable elastics. An elastic with improved strength and elastic properties in the CD is critical to personal care product applications.

The material described herein is a cast elastomeric film with improved physical properties made with a blend of polymers including a dispersed reinforcing elongated inclusion structure technology. The elastomeric film is a blend of a propylene-based olefinic elastomer, a terpolymer of ethylene, acrylic ester, and glycidyl methacrylate, and optionally an aliphatic polyester (plastic, or inelastic, component).

Various aspects of the present disclosure will now be described in more detail.

I. Thermoplastic Polyolefin Elastomer Composition

A. Polyolefin Elastomer Matrix

The polyolefin elastomer matrix can be a propylene-based olefinic elastomer such as VISTAMAXX 6102 polyolefin-based elastic.

Examples of polyolefin-based thermoplastic elastomers suitable for use in the elastomeric film include, among others, a crystalline polyolefin, for example, a homopolymer or a copolymer of an α-olefin having 1 to 20 carbon atoms, and including 1 to 12 carbon atoms.

Examples of polyolefin elastomers include polyolefinic copolymers described below.

(1) Copolymers of ethylene and not more than 20% by mol of α-olefins other than ethylene or vinyl monomers such as vinyl acetate and ethyl acrylate; examples include ethylene octene copolymer, available as ENGAGE 8407 and ENGAGE 8842 copolymer (Dow Chemical, Houston, Tex.).

(2) Random copolymers of propylene and not more than 20% by mol of α-olefins other than propylene (3) Block copolymers of propylene and not more than 30% by mol of α-olefins other than propylene.

(4) Random copolymers of 1-butene and not more than 20% by mol of α-olefins other than 1-butene.

(5) Random copolymers of 4-methyl-1-pentene and not more than 20% by mol of α-olefins other than 4-methyl-1-pentene.

Examples of the α-olefins include ethylene, propylene, 1-butene, 4-methyl-1-pentene, 1-hexene, and 1-octene.

Exemplary commercially-available polyolefin-based thermoplastic elastomers for use in the elastomeric film include VISTAMAXX propylene-based elastomer, available from ExxonMobil Chemical, Houston, Tex.; INFUSE olefin block copolymers, available from Dow Chemical Company, Midland, Mich.; VERSIFY propylene-ethylene copolymers such as VERSIFY 4200 and VERSIFY 4300 copolymers available from Dow Chemical Company, Midland, Mich.; ENGAGE ethylene octane copolymer, available from Dow Chemical, Houston, Tex.; and NOTIO 0040 and NOTIO 3560 polymers available from Mitsui Chemical (USA), New York, N.Y. In one particularly suitable aspect, the polyolefin-based thermoplastic elastomer is VISTAMAXX 6102FL elastomer.

Polyolefins typically constitute from about 60 wt. % to about 99 wt. %, in some aspects from about 60 wt. % to about 98 wt. %, and in some aspects, from about 80 wt. % to about 95 wt. % of the thermoplastic polyolefin elastomer composition.

The polyolefin elastomer can have a melting temperature of from about 100° C. to about 220° C., in some aspects from about 120° C. to about 200° C., and in some aspects, from about 140° C. to about 180° C. The melting temperature can be determined using differential scanning calorimetry ("DSC") in accordance with ASTM D-3417.

Of course, other polyolefins can also be employed in the composition of the present disclosure. In one aspect, for example, the polyolefin elastomer can be a copolymer of ethylene or propylene with another α-olefin, such as a $C_3$-$C_{20}$ α-olefin or $C_3$-$C_{12}$ α-olefin. Specific examples of suitable α-olefins include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene or propylene content of such copolymers can be from about 60 mole % to about 99 mole %, in some aspects from about 80 mole % to about 98.5 mole %, and in some aspects, from about 87 mole % to about 97.5 mole %. The α-olefin content can likewise range from about 1 mole % to about 40 mole %, in some aspects from about 1.5 mole % to about 15 mole %, and in some aspects, from about 2.5 mole % to about 13 mole %.

B. Nanoinclusion Additive

As used herein, the term "nanoinclusion additive" generally refers to a material that is capable of being dispersed within the polymer matrix in the form of discrete domains of a nano-scale size. For example, prior to stretching, the domains can have an average cross-sectional dimension of from about 1 to about 1000 nanometers, in some aspects from about 5 to about 800 nanometers, in some aspects from about 10 to about 500 nanometers, and in some aspects from about 20 to about 200 nanometers. The domains can have a variety of different shapes, such as elliptical, spherical, cylindrical, plate-like, tubular, etc. In one aspect, for example, the domains have a substantially elliptical shape. The domains can be elongated with an aspect ratio in the ranges from 5 to 1000, from 10 to 500, and from 10 to 100.

The nanoinclusion additive is typically employed in an amount of from about 0.05 wt. % to about 20 wt. %, in some aspects from about 0.1 wt. % to about 10 wt. %, and in some aspects, from about 0.5 wt. % to about 5 wt. % of the thermoplastic polyolefin elastomer composition, based on the weight of the continuous phase polyolefin elastomer matrix. The concentration of the nanoinclusion additive in the entire thermoplastic polyolefin elastomer composition can likewise be from about 0.01 wt. % to about 15 wt. %, in some aspects from about 0.05 wt. % to about 10 wt. %, and in some aspects, from about 0.3 wt. % to about 6 wt. % of the thermoplastic polyolefin elastomer composition.

The nanoinclusion additive is partially incompatible with the polyolefin elastomer in the sense that it can be substantially uniformly distributed within the polyolefin elastomer matrix, but in the form of discrete domains. Such partial incompatibility can be accomplished in a variety of ways. In certain aspects, for example, the nanoinclusion additive can possess a nonpolar component (e.g., olefin) that is compatible with the polyolefin elastomer matrix and allows it to become uniformly distributed therein. Nevertheless, the additive can also include a polar component that is incompatible with the polyolefin elastomer matrix, thereby allowing it to coalesce or segregate into discrete domains. Such a component can include low or high molecular weight polar molecular segments or blocks, ionic groups, charged or uncharged polar domains, and/or polar molecular groups. Alternatively, the additive can be entirely nonpolar in nature, but possess certain physical properties that still allow for discrete domains to be formed. For example, in certain aspects, the nanoinclusion additive can be compatible or miscible with the polyolefin elastomer above a certain temperature, but phase separate at temperatures lower than the critical solution temperature. In this manner, the nanoinclusion additive can form a stable blend with the polyolefin elastomer in the melt phase, but as the temperature decreases, the continuous phase crystallizes and segregates so that the nanoinclusion additive can phase separate, coalesce, and form separate nano-scale domains.

The particular state or form of the nanoinclusion additive is not critical so long as the desired domains can be formed. For example, in some aspects, the nanoinclusion additive can be in the form of a liquid or semi-solid at room temperature (e.g., 25° C.). Such a liquid can be readily dispersed in the matrix to form a metastable dispersion, and then quenched to preserve the domain size by reducing the temperature of the blend. The kinematic viscosity of such a liquid or semi-solid material is typically from about 0.7 to about 200 centistokes ("cs"), in some aspects from about 1 to about 100 cs, and in some aspects, from about 1.5 to about 80 cs, determined at 40° C. Suitable liquids or semi-solids can include, for instance, silicones, silicone-polyether copolymers, aliphatic polyesters, aromatic polyesters, alkylene glycols (e.g., ethylene glycol, diethylene glycol, triethylene glycol, tetraethylene glycol, propylene glycol, polyethylene glycol, polypropylene glycol, polybutylene glycol, etc.), alkane diols (e.g., 1,3-propanediol, 2,2-dimethyl-1,3-propanediol, 1,3-butanediol, 1,4-butanediol, 1,5-pentanediol, 1,6-hexanediol, 2,2,4-trimethyl-1,6 hexanediol, 1,3-cyclohexanedimethanol, 1,4-cyclohexanedimethanol, 2,2,4,4-tetramethyl-1,3-cyclobutanediol, etc.), amine oxides (e.g., octyldimethylamine oxide), fatty acid esters, fatty acid amides (e.g., oleamide, erucamide, stearamide, ethylene bis(stearamide), etc.), mineral, and vegetable oils, and so forth. One particularly suitable liquid or semi-solid is polyether polyol, such as commercially available under the trade name PLURIOL WI from BASF Corp.

In yet other aspects, the nanoinclusion additive is in the form of a solid that can be amorphous, crystalline, or semi-crystalline. For example, the nanoinclusion additive can be polymeric in nature and possess a relatively high molecular weight to help improve the melt strength and stability of the thermoplastic polyolefin elastomer composition. As indicated above, the nanoinclusion additive is partially incompatible with the polyolefin elastomer matrix. One example of such an additive is a microcrystalline polyolefin wax that is typically derived from ethylene and/or $C_3$-$C_{10}$-alk-1-enes, such as from propylene, 1-butene, 1-pentene, 1-hexene, 1-heptene, 1-octene, 1-nonene, and 1-decene. Microcrystalline waxes typically have a relatively low melting temperature, such as from about 30° C. to about 150° C., in some aspects from about 50° C. to about 140° C., and in some aspects, from about 80° C. to about 130° C. At such low melting temperatures, the wax can form a miscible blend with the polyolefin elastomer when in the melt phase, but as the temperature decreases and polymer crystalizes or solidifies, the wax will segregate and coalesce forming separate nano-scale domains.

Another example of a polymeric nanoinclusion additive is a functionalized polyolefin that contains a polar and nonpolar component. The polar component can, for example, be provided by one or more functional groups and the nonpolar component can be provided by an olefin. The olefin component of the nanoinclusion additive can generally be formed from any linear or branched α-olefin monomer, oligomer, or polymer (including copolymers) derived from an olefin monomer, such as described above. The functional group of the nanoinclusion additive can be any group, molecular segment and/or block that provides a polar component to the molecule and is not compatible with the polyolefin elastomer matrix. Examples of molecular segment and/or blocks not compatible with polyolefin can include acrylates, styrenics, polyesters, polyamides, etc. The functional group can have an ionic nature and include charged metal ions. Particularly suitable functional groups are maleic anhydride, maleic acid, fumaric acid, maleimide, maleic acid hydrazide, a reaction product of maleic anhydride and diamine, methylnadic anhydride, dichloromaleic anhydride, maleic acid amide, etc. Maleic anhydride modified polyolefins are particularly suitable for use in the present disclosure. Such modified polyolefins are typically formed by grafting maleic anhydride onto a polymeric backbone material. Such maleated polyolefins are available from E.I. du Pont de Nemours and Company under the designation FUSABOND, such as the P Series (chemically modified polypropylene), E Series (chemically modified polyethylene), C Series (chemically modified ethylene vinyl acetate), A Series (chemically modified ethylene acrylate copolymers or terpolymers), or N Series (chemically modified ethylene-propylene, ethylene-propylene diene monomer ("EPDM") or ethylene-octene). Alternatively, maleated polyolefins are also available from Chemtura Corp. under the designation POLYBOND, Eastman Chemical Company under the designation Eastman G series, and Arkema under the designation OREVAC.

In certain aspects, the polymeric nanoinclusion additive can also be reactive. One example of such a reactive nanoinclusion additive is a polyepoxide that contains, on average, at least two oxirane rings per molecule. Without intending to be limited by theory, it is believed that such polyepoxide molecules can undergo a reaction (e.g., chain extension, side chain branching, grafting, copolymer formation, etc.) with certain components of the composition to improve melt strength without significantly reducing glass transition temperature. The reactive additive can also provide compatibilization between the polyolefin elastomer and other more polar additives, such as microinclusion additives, and can improve the uniformity of dispersion and reduce the size of microinclusion additives. For example, as will be described in more detail below, certain aspects of the present disclosure can employ a polyester as a microinclusion additive. In such aspects, the reactive nanoinclusion additive can enable a nucleophilic ring-opening reaction via a carboxyl terminal group of the polyester (esterification) or via a hydroxyl group (etherification). Oxazoline side reactions can likewise occur to form esteramide moieties. Through such reactions, the molecular weight of a polyester microinclusion additive can be increased to counteract the degradation often observed during melt processing. Research for the present disclosure found that too much of a reaction can lead to crosslinking between polymer backbones. If such crosslinking is allowed to proceed to a significant extent, the resulting polymer blend can become brittle and difficult to process into a material with the desired strength and elongation properties.

In this regard, further research found that polyepoxides having a relatively low epoxy functionality can be particularly effective, quantifiable by its "epoxy equivalent weight." The epoxy equivalent weight reflects the amount of resin that contains one molecule of an epoxy group, and it can be calculated by dividing the number average molecular weight of the modifier by the number of epoxy groups in the molecule. The polyepoxide of the present disclosure typically has a number average molecular weight from about 7,500 to about 250,000 grams per mole, in some aspects from about 15,000 to about 150,000 grams per mole, and in some aspects, from about 20,000 to 100,000 grams per mole, with a polydispersity index typically ranging from 2.5 to 7. The polyepoxide can contain less than 50, in some aspects from 5 to 45, and in some aspects, from 15 to 40 epoxy groups. In turn, the epoxy equivalent weight can be less than about 15,000 grams per mole, in some aspects from about 200 to about 10,000 grams per mole, and in some aspects, from about 500 to about 7,000 grams per mole.

The polyepoxide can be a linear or branched, homopolymer or copolymer (e.g., random, graft, block, etc.) containing terminal epoxy groups, skeletal oxirane units, and/or pendent epoxy groups. The monomers employed to form such polyepoxides can vary. In one particular aspect, for example, the polyepoxide contains at least one epoxy-functional (meth)acrylic monomeric component. As used herein, the term "(meth)acrylic" includes acrylic and methacrylic monomers, as well as salts or esters thereof, such as acrylate and methacrylate monomers. For example, suitable epoxy-functional (meth)acrylic monomers can include, but are not limited to, those containing 1,2-epoxy groups, such as glycidyl acrylate and glycidyl methacrylate. Other suitable epoxy-functional monomers include allyl glycidyl ether, glycidyl ethacrylate, and glycidyl itoconate.

The polyepoxide typically has a relatively high molecular weight, as indicated above, so that it not only results in chain extension, but also helps to achieve the desired blend morphology. The resulting melt flow rate of the polymer is thus typically within a range of from about 10 to about 200 grams per 10 minutes, in some aspects from about 40 to about 150 grams per 10 minutes, and in some aspects, from about 60 to about 120 grams per 10 minutes, determined at a load of 2160 grams and at a temperature of 190° C.

The polyepoxide also typically includes at least one linear or branched α-olefin monomer, such as those having from 2 to 20 carbon atoms and preferably from 2 to 8 carbon atoms. Specific examples include ethylene, propylene, 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are ethylene and propylene. Another suitable monomer can include a (meth)acrylic monomer that is not epoxy-functional. Examples of such (meth)acrylic monomers can include methyl acrylate, ethyl acrylate, n-propyl acrylate, i-propyl acrylate, n-butyl acrylate, s-butyl acrylate, i-butyl acrylate, t-butyl acrylate, n-amyl acrylate, i-amyl acrylate, isobornyl acrylate, n-hexyl acrylate, 2-ethylbutyl acrylate, 2-ethylhexyl acrylate, n-octyl acrylate, n-decyl acrylate, methylcyclohexyl acrylate, cyclopentyl acrylate, cyclohexyl acrylate, methyl methacrylate, ethyl methacrylate, 2-hydroxyethyl methacrylate, n-propyl methacrylate, n-butyl methacrylate, i-propyl methacrylate, i-butyl methacrylate, n-amyl methacrylate, n-hexyl methacrylate, i-amyl methacrylate, s-butyl-methacrylate, t-butyl methacrylate, 2-ethylbutyl methacrylate, methylcyclohexyl methacrylate, cinnamyl methacrylate, crotyl methacrylate, cyclohexyl methacrylate, cyclopentyl methacrylate, 2-ethoxyethyl methacrylate, isobornyl methacrylate, etc., as well as combinations thereof.

In one particularly desirable aspect of the present disclosure, the polyepoxide is a terpolymer formed from an epoxy-functional (meth)acrylic monomeric component, α-olefin monomeric component, and non-epoxy functional (meth)acrylic monomeric component. For example, the polyepoxide can be poly(ethylene-co-methylacrylate-co-glycidyl methacrylate), which has the following structure:

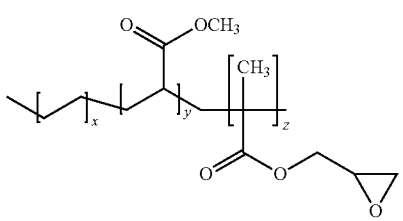

wherein, x, y, and z are 1 or greater.

The epoxy functional monomer can be formed into a polymer using a variety of known techniques. For example, a monomer containing polar functional groups can be grafted onto a polymer backbone to form a graft copolymer. Such grafting techniques are well known in the art and described, for instance, in U.S. Pat. No. 5,179,164. In other aspects, a monomer containing epoxy functional groups can be copolymerized with a monomer to form a block or random copolymer using known free radical polymerization techniques, such as high pressure reactions, Ziegler-Natta catalyst reaction systems, single site catalyst (e.g., metallocene) reaction systems, etc.

The relative portion of the monomeric component(s) can be selected to achieve a balance between epoxy-reactivity and melt flow rate. More particularly, high epoxy monomer contents can result in good reactivity, but too high of a content can reduce the melt flow rate to such an extent that the polyepoxide adversely impacts the melt strength of the polymer blend. Thus, in most aspects, the epoxy-functional (meth)acrylic monomer(s) constitute from about 1 wt. % to about 25 wt. %, in some aspects from about 2 wt. % to about 20 wt. %, and in some aspects, from about 4 wt. % to about 15 wt. % of the copolymer. The α-olefin monomer(s) can likewise constitute from about 55 wt. % to about 95 wt. %, in some aspects from about 60 wt. % to about 90 wt. %, and in some aspects, from about 65 wt. % to about 85 wt. % of the copolymer. When employed, other monomeric components (e.g., non-epoxy functional (meth)acrylic monomers) can constitute from about 5 wt. % to about 35 wt. %, in some aspects from about 8 wt. % to about 30 wt. %, and in some aspects, from about 10 wt. % to about 25 wt. % of the copolymer. One specific example of a suitable polyepoxide that can be used in the present disclosure is commercially available from Arkema as LOTADER AX8950 or AX8900 brand polyepoxide. LOTADER AX8950, for instance, has a melt flow rate of 70 to 100 g/10 min and has a glycidyl methacrylate monomer content of 7 wt. % to 11 wt. %, a methyl acrylate monomer content of 13 wt. % to 17 wt. %, and an ethylene monomer content of 72 wt. % to 80 wt. %. Another suitable polyepoxide is commercially available from DuPont ELVALOY PTW brand polyepoxide, which is a terpolymer of ethylene, butyl acrylate, and glycidyl methacrylate and has a melt flow rate of 12 g/10 min.

In addition to controlling the type and relative content of the monomers used to form the polyepoxide, the overall weight percentage can also be controlled to achieve the desired benefits. For example, if the modification level is too low, the desired increase in melt strength and mechanical properties cannot be achieved. Research for the present disclosure also found, however, that if the modification level is too high, processing can be restricted due to strong molecular interactions (e.g., crosslinking) and physical network formation by the epoxy functional groups. Thus, the polyepoxide is typically employed in an amount of from about 0.05 wt. % to about 10 wt. %, in some aspects from about 0.1 wt. % to about 8 wt. %, in some aspects from about 0.5 wt. % to about 5 wt. %, and in some aspects, from about 1 wt. % to about 3 wt. %, based on the weight of the polyolefin elastomers employed in the composition. The polyepoxide can also constitute from about 0.05 wt. % to about 10 wt. %, in some aspects from about 0.05 wt. % to about 8 wt. %, in some aspects from about 0.1 wt. % to about 5 wt. %, and in some aspects, from about 0.5 wt. % to about 3 wt. %, based on the total weight of the composition.

Other reactive nanoinclusion additives can also be employed in the present disclosure, such as oxazoline-functionalized polymers, cyanide-functionalized polymers, etc. When employed, such reactive nanoinclusion additives can be employed within the concentrations noted above for the polyepoxide. In one particular aspect, an oxazoline-grafted polyolefin can be employed that is a polyolefin grafted with an oxazoline ring-containing monomer. The oxazoline can include a 2-oxazoline, such as 2-vinyl-2-oxazoline (e.g., 2-isopropenyl-2-oxazoline), 2-fatty-alkyl-2-oxazoline (e.g., obtainable from the ethanolamide of oleic acid, linoleic acid, palmitoleic acid, gadoleic acid, erucic acid and/or arachidonic acid) and combinations thereof. In another aspect, the oxazoline can be selected from ricinoloxazoline maleinate, undecyl-2-oxazoline, soya-2-oxazoline, ricinus-2-oxazoline and combinations thereof, for example. In yet another aspect, the oxazoline is selected from 2-isopropenyl-2-oxazoline, 2-isopropenyl-4,4-dimethyl-2-oxazoline and combinations thereof.

In certain aspects of the present disclosure, multiple nanoinclusion additives can be employed in combination. For instance, a first nanoinclusion additive (e.g., polyepoxide) can be dispersed in the form of domains having an average cross-sectional dimension of from about 50 to about 500 nanometers, in some aspects from about 60 to about 400 nanometers, and in some aspects from about 80 to about 300 nanometers. A second nanoinclusion additive can also be dispersed in the form of domains that are smaller than the first nanoinclusion additive, such as those having an average cross-sectional dimension of from about 1 to about 50 nanometers, in some aspects from about 2 to about 45 nanometers, and in some aspects from about 5 to about 40 nanometers. When employed, the first and/or second nanoinclusion additives typically constitute from about 0.05 wt. % to about 20 wt. %, in some aspects from about 0.1 wt. % to about 10 wt. %, and in some aspects, from about 0.5 wt. % to about 5 wt. % of the thermoplastic polyolefin elastomer composition, based on the weight of the continuous phase (elastomer matrix(s)). The concentration of the first and/or second nanonclusion additives in the entire thermoplastic polyolefin elastomer composition can likewise be from about 0.01 wt. % to about 15 wt. %, in some aspects from about 0.05 wt. % to about 10 wt. %, and in some aspects, from about 0.1 wt. % to about 8 wt. % of the thermoplastic polyolefin elastomer composition.

Nanofillers can optionally be employed for the second nanoinclusion additive, examples of which can include carbon black, carbon nanotubes, carbon nanofibers, nanoclays, metal nanoparticles, nanosilica, nanoalumina, etc. Nanoclays are particularly suitable. The term "nanoclay" generally refers to nanoparticles of a clay material (a naturally occurring mineral, an organically modified mineral, or a synthetic nanomaterial), that typically have a platelet structure. Examples of nanoclays include, for instance, montmorillonite (2:1 layered smectite clay structure), bentonite (aluminium phyllosilicate formed primarily of montmorillonite), kaolinite (1:1 aluminosilicate having a platy structure and empirical formula of $Al_2Si_2O_5(OH)_4$), halloysite (1:1 aluminosilicate having a tubular structure and empirical formula of $Al_2Si_2O_5(OH)_4$), etc. An example of a suitable nanoclay is CLOISITE, which is a montmorillonite nanoclay and commercially available from Southern Clay Products, Inc. Other examples of synthetic nanoclays include but are not limited to a mixed-metal hydroxide nanoclay, layered double hydroxide nanoclay (e.g., sepiocite), laponite, hectorite, saponite, indonite, etc.

If desired, the nanoclay can contain a surface treatment to help improve compatibility with the elastomer matrix (e.g., polyester). The surface treatment can be organic or inorganic. In one aspect, an organic surface treatment is employed that is obtained by reacting an organic cation with the clay. Suitable organic cations can include, for instance, organoquaternary ammonium compounds that are capable of exchanging cations with the clay, such as dimethyl bis[hydrogenated tallow] ammonium chloride (2M2HT), methyl benzyl bis[hydrogenated tallow] ammonium chloride (MB2HT), methyl tris[hydrogenated tallow alkyl] chloride (M3HT), etc. Examples of commercially available organic nanoclays can include, for instance, DELLITE 43B (Laviosa Chimica of Livorno, Italy), which is a montmorillonite clay modified with dimethyl benzylhydrogenated tallow ammonium salt. Other examples include CLOISITE 25A and CLOISITE 30B (Southern Clay Products) and NANOFIL 919 (Süd Chemie) nanoclays. If desired, the nanofiller can be blended with a carrier resin to form a masterbatch that enhances the compatibility of the additive with the other polymers in the composition. Particularly suitable carrier resins include, for instance, polyesters (e.g., polylactic acid, polyethylene terephthalate, etc.); polyolefins (e.g., ethylene polymers, propylene polymers, etc.); and so forth, as described in more detail above.

Regardless of the material employed, the nanoinclusion additive is typically selected to have a certain viscosity (or melt flow rate) to ensure that the discrete domains and resulting inclusions can be adequately maintained. For example, if the viscosity of the nanoinclusion additive is too low (or melt flow rate is too high), it tends to flow and disperse uncontrollably through the continuous phase. This results in lamellar, plate-like domains or co-continuous phase structures that are difficult to maintain and also likely to prematurely fracture. Conversely, if the viscosity is too high (or melt flow rate is too low), it tends to clump together and form very large elliptical domains that are difficult to disperse during blending. This can cause uneven distribution of the nanoinclusion additive through the entirety of the continuous phase. For instance, the ratio of the melt flow rate of the polyolefin elastomer to the melt flow rate of a polymeric nanoinclusion additive, for instance, can be from about 0.2 to about 8, in some aspects from about 0.5 to about 6, and in some aspects, from about 1 to about 5. The nanoinclusion additive can, for example, have a melt flow rate (on a dry basis) of from about 0.1 to about 100 grams per 10 minutes, in some aspects from about 0.5 to about 50 grams per 10 minutes, and in some aspects from about 5 to about 15 grams per 10 minutes, determined at a load of 2160 grams and at a temperature at least about 40° C. above the melting temperature (e.g., at 190° C.) in accordance with ASTM D1238. The polyolefin elastomer can likewise have a melt flow rate (on a dry basis) of from about 0.5 to about 80 grams per 10 minutes, in some aspects from about 1 to about 40 grams per 10 minutes, and in some aspects, from about 5 to about 20 grams per 10 minutes, determined at a load of 2160 grams and at a temperature at least about 40° C. above the melting temperature (e.g., at 230° C.) in accordance with ASTM D1238.

C. Microinclusion Additive

Although not required, the composition of the present disclosure can also employ a microinclusion additive. As used herein, the term "microinclusion additive" generally refers to any material that is capable of being dispersed within the polyolefin elastomer matrix in the form of discrete domains of a micro-scale size. For example, prior to stretching, the domains can have an average cross-sectional dimension of from about 0.01 µm to about 100 µm, in some aspects about 0.01 µm to about 25 µm, in some aspects from about 0.1 µm to about 20 µm, and in some aspects from about 1 µm to about 10 µm.

The particular nature of the microinclusion additive is not critical, and can include liquids, semi-solids, or solids (e.g., amorphous, crystalline, or semi-crystalline). In certain aspects, the microinclusion additive is polymeric in nature and possesses a relatively high molecular weight to help improve the melt strength and stability of the thermoplastic polyolefin elastomer composition. Typically, the microinclusion additive polymer can be generally incompatible with the elastomer matrix. In this manner, the additive can better become dispersed as discrete phase domains within a continuous phase of the elastomer matrix. The discrete domains are capable of absorbing energy and stress- or load-bearing. This increases the overall toughness and strength of the resulting material. The domains can have a variety of different shapes, such as elliptical, spherical, cylindrical, plate-like, tubular, etc. In one aspect, for example, the domains have a substantially elliptical shape. The domains can be elongated with an aspect ratio in the ranges from 5 to 1000, from 10 to 500, and from 10 to 100. The physical dimension of an individual domain is typically small enough to minimize the propagation of cracks through the polymeric material upon the application of an external stress, but large enough to initiate microscopic elastic deformation and allow for shear zones at and around particle inclusions.

The microinclusion additive can have a certain melt flow rate (or viscosity) to ensure that the discrete domains and resulting inclusions can be adequately maintained. For example, if the melt flow rate of the additive is too high, it tends to flow and disperse uncontrollably through the continuous phase. This results in lamellar, plate-like domains or co-continuous phase structures that are difficult to maintain and also likely to prematurely fracture. Conversely, if the melt flow rate of the additive is too low, it tends to clump together and form very large elliptical domains that are difficult to disperse during blending. This can cause uneven distribution of the additive through the entirety of the continuous phase. In this regard, research for the present disclosure found that the ratio of the melt flow rate of the microinclusion additive to the melt flow rate of the elastomer matrix is typically from about 0.5 to about 10, in some aspects from about 1 to about 8, and in some aspects, from about 2 to about 6. The microinclusion additive can, for example, have a melt flow rate of from about 5 to about 200 grams per 10 minutes, in some aspects from about 20 to about 150 grams per 10 minutes, and in some aspects, from about 40 to about 100 grams per 10 minutes, determined at a load of 2160 grams and at a temperature at least about 40° C. above its melting temperature (e.g., 210° C.).

While a wide variety of microinclusion additives can be employed that have the properties identified above, particularly suitable examples of such additives can include styrenic copolymers (e.g., styrene-butadiene-styrene, styrene-isoprene-styrene, styrene-ethylene-propylene-styrene, styrene-ethylene-butadiene-styrene, etc.); fluoropolymers, such as polyvinyl chloride (PVC), polytetrafluoroethylene (PTFE), polychlorotrifluoroethylene (PCTFE), etc.; polyvinyl alcohols; polyvinyl acetates; polyesters, such as aliphatic polyesters, such as polycaprolactone, polyesteramides, polylactic acid (PLA) and its copolymers, polyglycolic acid, polyalkylene carbonates (e.g., polyethylene carbonate), poly-3-hydroxybutyrate (PHB), poly-3-hydroxyvalerate (PHV), poly-3-hydroxybutyrate-co-4-hydroybutyrate, poly-3-hydroxybutyrate-co-3-hydroxyvalerate copolymers (PHBV), poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, and succinate-based aliphatic polymers (e.g., polybutylene succinate, polybutylene succinate adipate, polyethylene succinate, etc.), aliphatic-aromatic copolyesters (e.g., polybutylene adipate terephthalate, polyethylene adipate terephthalate, polyethylene adipate isophthalate, polybutylene adipate isophthalate, etc.), aromatic polyesters (e.g., polyethylene terephthalate, polybutylene terephthalate, etc.); and so forth.

Particularly suitable are microinclusion additives that are generally rigid in nature to the extent that they have a relatively high glass transition temperature. For example, the glass transition temperature ("$T_g$") can be about 0° C. or more, in some aspects from about 5° C. to about 100° C., in some aspects from about 30° C. to about 80° C., and in some aspects, from about 50° C. to about 75° C. The glass transition temperature can be determined by dynamic mechanical analysis in accordance with ASTM E1640-09.

One particularly suitable rigid polyester is polylactic acid that can generally be derived from monomer units of any isomer of lactic acid, such as levorotory-lactic acid ("L-lactic acid"), dextrorotatory-lactic acid ("D-lactic acid"), meso-lactic acid, or mixtures thereof. Monomer units can also be formed from anhydrides of any isomer of lactic acid, including L-lactide, D-lactide, meso-lactide, or mixtures thereof. Cyclic dimers of such lactic acids and/or lactides can also be employed. Any known polymerization method, such as polycondensation or ring-opening polymerization, can be used to polymerize lactic acid. A small amount of a chain-extending agent (e.g., a diisocyanate compound, an epoxy compound or an acid anhydride) can also be employed. The polylactic acid can be a homopolymer or a copolymer, such as one that contains monomer units derived from L-lactic acid and monomer units derived from D-lactic acid. Although not required, the rate of content of one of the monomer unit derived from L-lactic acid and the monomer unit derived from D-lactic acid is preferably about 85 mole % or more, in some aspects about 90 mole % or more, and in some aspects, about 95 mole % or more. Multiple polylactic acids, each having a different ratio between the monomer unit derived from L-lactic acid and the monomer unit derived from D-lactic acid, can be blended at an arbitrary percentage. Of course, polylactic acid can also be blended with other types of polymers (e.g., polyolefins, polyesters, etc.).

In one particular aspect, the polylactic acid has the following general structure:

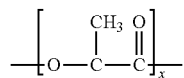

One specific example of a suitable polylactic acid polymer that can be used in the present disclosure is commercially available from Biomer, Inc. of Krailling, Germany) under the name BIOMER L9000. Other suitable polylactic acid polymers are commercially available from Natureworks LLC of Minnetonka, Minn. (NATUREWORKS) or Mitsui Chemical (LACEA). Still other suitable polylactic acids can be described in U.S. Pat. Nos. 4,797,468; 5,470,944; 5,770,682; 5,821,327; 5,880,254; and 6,326,458, which are incorporated herein in their entirety by reference thereto for all purposes.

The polylactic acid typically has a number average molecular weight ("$M_n$") ranging from about 40,000 to about 180,000 grams per mole, in some aspects from about 50,000 to about 160,000 grams per mole, and in some aspects, from about 80,000 to about 120,000 grams per mole. Likewise, the polymer also typically has a weight average molecular weight ("$M_w$") ranging from about 80,000 to about 250,000 grams per mole, in some aspects from about 100,000 to about 200,000 grams per mole, and in some aspects, from about 110,000 to about 160,000 grams per mole. The ratio of the weight average molecular weight to the number average molecular weight ("$M_w/M_n$"), i.e., the "polydispersity index", is also relatively low. For example, the polydispersity index typically ranges from about 1.0 to about 3.0, in some aspects from about 1.1 to about 2.0, and in some aspects, from about 1.2 to about 1.8. The weight and number average molecular weights can be determined by methods known to those skilled in the art.

Some types of neat polyesters (e.g., polylactic acid) can absorb water from the ambient environment such that it has a moisture content of about 500 to 600 parts per million ("ppm"), or even greater, based on the dry weight of the starting polylactic acid. Moisture content can be determined in a variety of ways as is known in the art, such as in accordance with ASTM D 7191-05, such as described below. Because the presence of water during melt processing can hydrolytically degrade the polyester and reduce its molecular weight, it is sometimes desired to dry the polyester prior to blending. In most aspects, for example, it is desired that the renewable polyester have a moisture content of about 300 parts per million ("ppm") or less, in some aspects about 200 ppm or less, in some aspects from about 1 to about 100 ppm prior to blending with the microinclusion additive. Drying of the polyester can occur, for instance, at a temperature of from about 50° C. to about 100° C., and in some aspects, from about 70° C. to about 80° C.

Regardless of the materials employed, the relative percentage of the microinclusion additive in the thermoplastic polyolefin elastomer composition is selected to achieve the desired properties without significantly impacting the resulting composition. For example, the microinclusion additive is typically employed in an amount of from about 1 wt. % to about 30 wt. %, in some aspects from about 2 wt. % to about 25 wt. %, and in some aspects, from about 5 wt. % to about 20 wt. % of the thermoplastic polyolefin elastomer composition, based on the weight of the polyolefin elastomer matrix employed in the composition. The concentration of the microinclusion additive in the entire thermoplastic polyolefin elastomer composition can likewise constitute from about 0.1 wt. % to about 30 wt. %, in some aspects from about 0.5 wt. % to about 25 wt. %, and in some aspects, from about 1 wt. % to about 20 wt. %.

D. Other Components

A wide variety of ingredients can be employed in the composition for a variety of different reasons. For instance, in one particular aspect, a compatibilizer can be employed to improve interfacial adhesion and reduce the interfacial tension between the domain and the matrix, thus allowing the formation of smaller domains during mixing. Examples of suitable compatibilizers can include, for instance, copolymers functionalized with epoxy or maleic anhydride chemical moieties. An example of a maleic anhydride compatibilizer is polypropylene-grafted-maleic anhydride, which is commercially available from Arkema under the trade names OREVAC 18750 and OREVAC CA 100. When employed, compatibilizers can constitute from about 0.05 wt. % to about 10 wt. %, in some aspects from about 0.1 wt. % to about 8 wt. %, and in some aspects, from about 0.5 wt. % to about 5 wt. % of the thermoplastic polyolefin elastomer composition, based on the weight of the continuous phase polyolefin elastomer matrix. The compatibilizer helps with the "connectivity" between the plastic inclusion phase and the elastomeric matrix phase, and is what helps to prevent permanent voiding/detachment when stretched in the CD, though there is some minimal amount of partial detachment in the MD.

The composition can also include an interphase modifier in the thermoplastic polyolefin elastomer composition to help reduce the degree of friction and connectivity between the nanoinclusion and/or microinclusion additives and polyolefin elastomer matrix, and thus enhance the degree and uniformity of debonding. In this manner, the inclusions can become distributed in a more homogeneous fashion throughout the composition. The modifier can be in a liquid or semi-solid form at room temperature (e.g., 25° C.) so that it possesses a relatively low viscosity, allowing it to be more readily incorporated into the thermoplastic polyolefin elastomer composition and to easily migrate to the polymer surfaces. By reducing physical forces at the interfaces of the polyolefin elastomer matrix and the additive, it is believed that the low viscosity, hydrophobic nature of the modifier can help facilitate debonding. As used herein, the term "hydrophobic" typically refers to a material having a contact angle of water in air of about 40° or more, and in some cases, about 60° or more. In contrast, the term "hydrophilic" typically refers to a material having a contact angle of water in air of less than about 40°. One suitable test for measuring the contact angle is ASTM D5725-99 (2008).

Although not required, the interphase modifier can be particularly suitable in aspects in which a microinclusion additive is employed and in which the nanoinclusion additive is a solid (e.g., polymeric material). Suitable hydrophobic, low viscosity interphase modifiers can include, for instance, the liquids and/or semi-solids referenced above. One particularly suitable interphase modifier is polyether polyol, such as commercially available under the trade name PLURIOL WI from BASF Corp. Suitable interphase modifiers can include polyester, PLA, polystyrene, polyurethane, polyolefin, polyamide, and nylon.

When employed, the interphase modifier can constitute from about 0.1 wt. % to about 20 wt. %, in some aspects from about 0.5 wt. % to about 15 wt. %, and in some aspects, from about 1 wt. % to about 10 wt. % of the thermoplastic polyolefin elastomer composition, based on the weight of the continuous phase polyolefin elastomer matrix. The concentration of the interphase modifier in the entire thermoplastic polyolefin elastomer composition can likewise constitute from about 0.05 wt. % to about 20 wt. %, in some aspects from about 0.1 wt. % to about 15 wt. %, and in some aspects, from about 0.5 wt. % to about 10 wt. %. In the amounts noted above, the interphase modifier has a character that enables it to readily migrate to the interfacial surface of the polymers and facilitate debonding without disrupting the overall melt properties of the thermoplastic polyolefin elastomer composition. For example, the melt flow rate of the thermoplastic polyolefin elastomer composition can also be similar to that of the polyolefin elastomer matrix. For example, the melt flow rate of the composition (on a dry basis) can be from about 0.1 to about 250 grams per 10 minutes, in some aspects from about 0.5 to about 200 grams per 10 minutes, and in some aspects, from about 5 to about 150 grams per 10 minutes, determined at a load of 2160 grams and at 190° C. in accordance with ASTM D1238.

Other suitable materials that can also be used in the thermoplastic polyolefin elastomer composition, such as catalysts, antioxidants, stabilizers, surfactants, waxes, solid solvents, nucleating agents, particulates, nanofillers, and other materials added to enhance the processability and mechanical properties of the thermoplastic polyolefin elastomer composition.

II. Blending

To form the thermoplastic polyolefin elastomer composition, the components are typically blended together using any of a variety of known techniques. In one aspect, for example, the components can be supplied separately or in combination. For instance, the components can first be dry mixed together to form an essentially homogeneous dry mixture, and they can likewise be supplied either simultaneously or in sequence to a melt processing device that dispersively blends the materials. Batch and/or continuous melt processing techniques can be employed. For example, a mixer/kneader, Banbury mixer, Farrel continuous mixer, single-screw extruder, twin-screw extruder, roll mill, etc., can be utilized to blend and melt process the materials. Particularly suitable melt processing devices can be a co-rotating, twin-screw extruder (e.g., ZSK-30 extruder available from Werner & Pfleiderer Corporation of Ramsey, N.J. or a THERMO PRISM USALAB 16 brand extruder available from Thermo Electron Corp., Stone, England). Such extruders can include feeding and venting ports and provide high intensity distributive and dispersive mixing. For example, the components can be fed to the same or different feeding ports of the twin-screw extruder and melt blended to form a substantially homogeneous melted mixture. If desired, other additives can also be injected into the polymer melt and/or separately fed into the extruder at a different point along its length.

Regardless of the particular processing technique chosen, the resulting melt blended composition typically contains nano-scale domains of the nanoinclusion additive and optionally micro-scale domains of the microinclusion additive. The degree of shear/pressure and heat can be controlled to ensure sufficient dispersion, but not so high as to adversely reduce the size of the domains so that they are incapable of achieving the desired properties. For example, blending typically occurs at a temperature of from about 180° C. to about 300° C., in some aspects from about 185° C. to about 250° C., and in some aspects, from about 190° C. to about 240° C. Likewise, the apparent shear rate during melt processing can range from about 10 seconds$^{-1}$ to about 3000 seconds$^{-1}$, in some aspects from about 50 seconds$^{-1}$ to about 2000 seconds$^{-1}$, and in some aspects, from about 100 seconds$^{-1}$ to about 1200 seconds$^{-1}$. The apparent shear rate can be equal to $4Q/R^3$, where Q is the volumetric flow rate ("m$^3$/s") of the polymer melt and R is the radius ("m") of the capillary (e.g., extruder die) through which the melted polymer flows. Of course, other variables, such as the residence time during melt processing, which is inversely proportional to throughput rate, can also be controlled to achieve the desired degree of homogeneity.

To achieve the desired shear conditions (e.g., rate, residence time, shear rate, melt processing temperature, etc.), the speed of the extruder screw(s) can be selected with a certain range. Generally, an increase in product temperature is observed with increasing screw speed due to the additional mechanical energy input into the system. For example, the screw speed can range from about 50 to about 600 revolutions per minute ("rpm"), in some aspects from about 70 to about 500 rpm, and in some aspects, from about 100 to about 300 rpm. This can result in a temperature that is sufficiently high to disperse the nanoinclusion additive without adversely impacting the size of the resulting domains. The melt shear rate, and in turn the degree to which the additives are dispersed, can also be increased through the use of one or more distributive and/or dispersive mixing elements within the mixing section of the extruder. Suitable distributive mixers for single screw extruders can include, for instance, Saxon, Dulmage, Cavity Transfer mixers, etc. Likewise, suitable dispersive mixers can include Blister ring, Leroy/Maddock, CRD mixers, etc. As is well known in the art, the mixing can be further improved by using pins in the barrel that create a folding and reorientation of the polymer melt, such as those used in Buss Kneader extruders, Cavity Transfer mixers, and Vortex Intermeshing Pin (VIP) mixers.

III. Film Construction

Any known technique can be used to form a film from the composition, including blowing, casting, flat die extruding, etc. In one particular aspect, the film can be formed by a blown process in which a gas (e.g., air) is used to expand a bubble of the extruded polymer blend through an annular die. The bubble is then collapsed and collected in flat film form. Processes for producing blown films are described, for instance, in U.S. Pat. No. 3,354,506 to Raley; U.S. Pat. No. 3,650,649 to Schippers; and U.S. Pat. No. 3,801,429 to Schrenk et al., as well as U.S. Patent Application Publication Nos. 2005/0245162 to McCormack, et al. and 2003/0068951 to Boggs, et al. In yet another aspect, however, the film is formed using a casting technique.

In one method for forming a cast film, the raw materials are supplied to the extruder from a hopper and then cast onto a casting roll to form a single-layered precursor film. If a multilayered film is to be produced, the multiple layers are co-extruded together onto the casting roll. The casting roll can optionally be provided with embossing elements to impart a pattern to the film. Typically, the casting roll is kept at temperature sufficient to solidify and quench the sheet as it is formed, such as from about 10° C. to 60° C. If desired, a vacuum box can be positioned adjacent to the casting roll to help keep the precursor film close to the surface of the roll. Additionally, air knives or electrostatic pinners can help force the precursor film against the surface of the casting roll as it moves around a spinning roll. An air knife is a device known in the art that focuses a stream of air at a very high flow rate to pin the edges of the film.

The resulting film can then be wound and stored on a take-up roll. Various additional potential processing and/or finishing steps known in the art, such as slitting, treating, aperturing, printing graphics, or lamination of the film with other layers (e.g., nonwoven web materials), can be performed without departing from the spirit and scope of the disclosure.

The film of the present disclosure can be mono- or multi-layered (e.g., from 2 to 20 layers, and in some aspects, from 3 to 10 layers). For example, a multi-layered film can contain at least one core layer that is positioned adjacent to at least one outer layer. In one aspect, for example, it can be desirable to employ first and second outer layers that sandwich the core layer. The core layer(s) typically constitute a substantial portion of the weight of the film, such as from about 50 wt. % to about 99 wt. %, in some aspects from about 55 wt. % to about 90 wt. %, and in some aspects, from about 60 wt. % to about 85 wt. % of the film. The outer layer(s) can likewise constitute from about 1 wt. % to about 50 wt. %, in some aspects from about 10 wt. % to about 45 wt. %, and in some aspects, from about 15 wt. % to about 40 wt. % of the film. Each outer layer can also have a thickness of from about 0.1 to about 10 micrometers, in some aspects from about 0.5 to about 5 micrometers, and in some aspects, from about 1 to about 2.5 micrometers. Likewise, the core layer can have a thickness of from about from about 1 to about 40 micrometers, in some aspects from about 2 to about 25 micrometers, and in some aspects, from about 5 to about 20 micrometers.

The thermoplastic polyolefin elastomer composition of the present disclosure can be employed in any layer of the film, including the core layer and/or the outer layer. In one aspect, for example, the core layer is formed from the composition of the present disclosure and the outer layer(s) are formed from the composition or from an additional polymer material. Likewise, in other possible aspects, one or more of the outer layers are formed from the composition of the present disclosure and the core layer is formed from an additional polymer material. When employed, the additional material can include any type of polymer, such as polyolefins (e.g., polyethylene, polypropylene, etc.), polyesters, polyamides, styrenic copolymers, polyurethanes, polyvinyl acetate, polyvinyl alcohol, etc.

If desired, the film can also be laminated to one or more nonwoven web facings to reduce the coefficient of friction and enhance the cloth-like feel of the composite surface. Exemplary polymers for use in forming nonwoven web facings can include, for instance, polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; copolymers thereof; and so forth. If desired, renewable polymers, such as those described above, can also be employed. Synthetic or natural cellulosic polymers can also be used, including but not limited to, cellulosic esters; cellulosic ethers; cellulosic nitrates; cellulosic acetates; cellulosic acetate butyrates; ethyl cellulose; regenerated celluloses, such as viscose, rayon, and so forth. It should be noted that the polymer(s) can also contain other additives, such as processing aids or treatment compositions to impart desired properties to the fibers, residual amounts of solvents, pigments or colorants, and so forth.

Monocomponent and/or multicomponent fibers can be used to form the nonwoven web facing. Monocomponent fibers are generally formed from a polymer or blend of polymers extruded from a single extruder. Multicomponent fibers are generally formed from two or more polymers (e.g., bicomponent fibers) extruded from separate extruders. The polymers can be arranged in substantially constantly positioned distinct zones across the cross-section of the fibers. The components can be arranged in any desired configuration, such as sheath-core, side-by-side, pie, island-in-the-sea, three island, bull's eye, or various other arrangements known in the art. Multicomponent fibers having various irregular shapes can also be formed.

Fibers of any desired length can be employed, such as staple fibers, continuous fibers, etc. In one particular aspect, for example, staple fibers can be used that have a fiber length in the range of from about 1 to about 150 millimeters, in some aspects from about 5 to about 50 millimeters, in some aspects from about 10 to about 40 millimeters, and in some aspects, from about 10 to about 25 millimeters. Although not required, carding techniques can be employed to form fibrous layers with staple fibers as is well known in the art. For example, fibers can be formed into a carded web by placing bales of the fibers into a picker that separates the fibers. Next, the fibers are sent through a combing or carding unit that further breaks apart and aligns the fibers in the machine direction so as to form a machine direction-oriented fibrous nonwoven web. The carded web can then be bonded using known techniques to form a bonded carded nonwoven web.

If desired, the nonwoven web facing used to form the nonwoven composite can have a multi-layer structure. Suitable multi-layered materials can include, for instance, spunbond/meltblown/spunbond (SMS) laminates and spunbond/meltblown (SM) laminates. Another example of a multi-layered structure is a spunbond web produced on a multiple spin bank machine in which a spin bank deposits fibers over a layer of fibers deposited from a previous spin bank. Such an individual spunbond nonwoven web can also be thought of as a multi-layered structure. In this situation, the various layers of deposited fibers in the nonwoven web can be the same, or they can be different in basis weight and/or in terms of the composition, type, size, level of crimp, and/or shape of the fibers produced. As another example, a single nonwoven web can be provided as two or more individually produced layers of a spunbond web, a carded web, etc., that have been bonded together to form the nonwoven web. These individually produced layers can differ in terms of production method, basis weight, composition, and fibers as discussed above. A nonwoven web facing can also contain an additional fibrous component such that it is considered a composite. For example, a nonwoven web can be entangled with another fibrous component using any of a variety of entanglement techniques known in the art (e.g., hydraulic, air, mechanical, etc.). In one aspect, the nonwoven web is integrally entangled with cellulosic fibers using hydraulic entanglement. A typical hydraulic entangling process utilizes high pressure jet streams of water to entangle fibers to form a highly entangled consolidated fibrous structure, e.g., a nonwoven web. The fibrous component of the composite can contain any desired amount of the resulting substrate.

The inclusions (e.g., nanoinclusions, microinclusions, or both), regardless of their particular size can be distributed in a substantially homogeneous fashion throughout the material.

The film resulting from the process described herein tends to have its inclusion domains largely aligned; the long axes of the domains are substantially parallel in the MD. When the film is stretched in the CD, however, the elongated inclusions reversibly re-orient such that their long axes are substantially parallel in the CD. When the stretched film is allowed to relaxed, the elongated inclusions re-orient back to being substantially parallel in the MD. This reversible re-orientation allows the inclusions to provide strength and rigidity in both the MD and the CD without sacrificing elastic properties.

Specific examples are made with VISTAMAXX 6102 polyolefin-based elastic as the elastomer, LOTADER AX8900 polyolefin-based epoxy resin as the terpolymer, and thermoplastic polylactic acid (PLA). Blends were 92.5/7.5 or 90/5/5.

Physical property improvement includes increased MD peak load and tensile strength and increased CD peak load, elongation at peak, and tensile strength. A nearly 50% improvement in the CD tensile strength is especially surprising for the blend that includes a plastic component, such as PLA, with no significant degradation in CD percent set.

Scanning electron microscope (SEM) studies showed the dispersed reinforcing elongated inclusion structure is evident in the film, with micro- and nano-domains around the LOTADER polyolefin-based epoxy resin or LOTADER polyolefin-based epoxy resin/PLA inclusions. Optical microscopy demonstrated that these micro-domains reversibly re-orient during CD stretching, which helps to maintain good CD elastic properties.

The dispersed reinforcing elongated inclusion structures in the thermoplastic polyolefin elastomer film allow a step change in material usage and performance. This structure provides a variety of additional benefits to an elastic film including improved tensile strength and elongation-to-break characteristics, and higher CD tensile strength, peak load, and elongation-to-break with substantially the same permanent set as 100% polyolefin elastomer after multiple stress-strain extension cycles.

In prior attempts, a plastic polymer system blended with an elastic polymer component results in improved toughness of the plastic-based polymer with decreased ultimate tensile strength. Conversely, an elastic polymer system blended with a plastic component results in increased tensile strength with higher hysteresis and permanent set. In a typical example, polymer resin acrylonitrile-butadiene-styrene (ABS) copolymer system is blended with plasticized polyvinylchloride (PVC). It is also known that an elastic film made from the extrusion cast process shows better strength and elasticity in the MD as compared to the CD, as shown in Table 1 for a polyolefin-based elastic such as VISTAMAXX polyolefin-based elastic from ExxonMobil. There are no reported cast polyolefin-based elastic polymeric films blended with plastic components that have a better tensile strength and elasticity in the CD than in the MD. An elastic with better strength and elastic properties in the CD is an important improvement, particularly for personal care product applications.

The present disclosure can be better understood with reference to the following examples.

Test Methods

Melt Flow Rate:

The melt flow rate ("MFR") is the weight of a polymer (in grams) forced through an extrusion rheometer orifice (0.0825-inch diameter) when subjected to a load of 2160 grams in 10 minutes, typically at 190° C., 210° C., or 230° C. Unless otherwise indicated, melt flow rate is measured in accordance with ASTM Test Method D1238 with a Tinius Olsen Extrusion Plastometer.

Thermal Properties:

The glass transition temperature ($T_g$) can be determined by dynamic mechanical analysis (DMA) in accordance with ASTM E1640-09. A Q800 instrument from TA Instruments can be used. The experimental runs can be executed in tension/tension geometry, in a temperature sweep mode in the range from −120° C. to 150° C. with a heating rate of 3° C./min. The strain amplitude frequency can be kept constant (2 Hz) during the test. Three (3) independent samples can be tested to get an average glass transition temperature, which is defined by the peak value of the tan δ curve, wherein tan δ is defined as the ratio of the loss modulus to the storage modulus (tan δ=E"/E').

The melting temperature can be determined by differential scanning calorimetry (DSC). The differential scanning calorimeter can be a DSC Q100 Differential Scanning calorimeter, which was outfitted with a liquid nitrogen cooling accessory and with a UNIVERSAL ANALYSIS 2000 (version 4.6.6) analysis software program, both of which are available from T.A. Instruments Inc. of New Castle, Del. To avoid directly handling the samples, tweezers or other tools are used. The samples are placed into an aluminum pan and weighed to an accuracy of 0.01 milligram on an analytical balance. A lid is crimped over the material sample onto the pan. Typically, the resin pellets are placed directly in the weighing pan.

The differential scanning calorimeter is calibrated using an indium metal standard and a baseline correction is performed, as described in the operating manual for the differential scanning calorimeter. A material sample is placed into the test chamber of the differential scanning calorimeter for testing, and an empty pan is used as a reference. All testing is run with a 55-cubic centimeter per minute nitrogen (industrial grade) purge on the test chamber. For resin pellet samples, the heating and cooling program is a 2-cycle test that began with an equilibration of the chamber to −30° C., followed by a first heating period at a heating rate of 10° C. per minute to a temperature of 200° C., followed by equilibration of the sample at 200° C. for 3 minutes, followed by a first cooling period at a cooling rate of 10° C. per minute to a temperature of −30° C., followed by equilibration of the sample at −30° C. for 3 minutes, and then a second heating period at a heating rate of 10° C. per minute to a temperature of 200° C. All testing is run with a 55-cubic centimeter per minute nitrogen (industrial grade) purge on the test chamber.

The results are evaluated using the UNIVERSAL ANALYSIS 2000 analysis software program that identified and quantified the glass transition temperature ($T_g$) of inflection, the endothermic and exothermic peaks, and the areas under the peaks on the DSC plots. The glass transition temperature is identified as the region on the plot-line where a distinct change in slope occurred, and the melting temperature is determined using an automatic inflection calculation.

Film Tensile Properties:

Films can be tested for tensile properties (peak stress, modulus, strain at break, and energy per volume at break). These measurements are performed using a strip elongation test that is substantially in accordance with the specifications in ASTM D5459-95. Specifically, the test uses two clamps each having two jaws with each jaw having a facing in contact with the sample. The clamps hold the material in the same plane, usually vertically, separated by 1 inch and move the cross head at a specific rate of extension. The sample size is 4 inches by 3/8 inches (101.6 mm by 9.525 mm) with a jaw facing height of 1 inch and width of 3 inches and at a cross-head displacement rate of 20 in/min. The specimen is clamped in a MTS (Mechanical Test Systems) electromechanical test frame that has data acquisition capability. The test is conducted at ambient condition both in cross direction and machine direction (CD & MD). Results are reported as an average of at least five specimens.

More particularly, the materials were tested using a cyclical testing procedure to determine percent set. In particular, 3-cycle testing was utilized to 150 percent defined elongation. The test was conducted under ambient conditions. For this test, the sample size was 3/8 inch (9.525 millimeters) by 4 inches (101.6 millimeters). The grip size was 3 inches (76 millimeters) in width and the grip separation was 1 inches. The samples were loaded such that the machine direction or cross direction of the sample was in the vertical direction, depending on the desired orientation. A preload of approximately 20 to 30 grams was set. The test pulled the sample to 150 percent elongation at a speed of 20 inches (508 millimeters) per minute, then returned the sample to zero elongation at a speed of 20 inches (508 millimeters) per minute. Thereafter, percent set was determined as percent elongation at which stress becomes zero in a stress-% elongation plot during return cycle. In other aspects, after each cycle, percent set value is recorded after the $1^{st}$ cycle (50%), the $2^{nd}$ cycle (100%), and the $3^{rd}$ cycle (150%), respectively. Only the percent set value after $3^{rd}$ 150% cycle was used. Typically the value of percent set is same after 3-cycle testing up to 150% and after 1-cycle testing up to 150%.

EXAMPLES

Table 1 shows the basic physical properties of 100% VISTAMAXX polyolefin-based elastic film and films with blended dispersed reinforcing elongated inclusion structure formulations (in various examples, 7.5% LOTADER polyolefin-based epoxy resin, 5% LOTADER polyolefin-based epoxy resin, and/or 5% PLA). All the films were made from an extrusion casting process with the following extrusion conditions. A 25 mm twist screw extruder from Nanjing Giaon with L/D=30, 5 zones (180° F., 230° F., 300° F., 340° F., 340° F., 340° F.), die, 355° F., a speed of 180 rpm, a die pressure of 600 psi, a feeding rate of 4 lb/hr, and the chill roll on at 5.6 fpm. The film basis weight was 60 gsm.

For comparison Sample 1, 100% VISTAMAXX 6102 FL polyolefin-based elastic film was produced and tested. For experimental Sample 2, VISTAMAXX 6102 FL grade polyolefin-based elastic was compounded with 7.5% (wt) LOTADER polyolefin-based epoxy resin. For experimental Sample 3, VISTAMAXX 6102 FL grade polyolefin-based elastic was compounded with 5% (wt) LOTADER polyolefin-based epoxy resin and 5% PLA. The blends were compounded with the following conditions:

TABLE 1

Physical properties of VISTAMAXX polyolefin-based elastic film and dispersed reinforcing elongated inclusion structure VISTAMAXX polyolefin-based elastic films

| | | Peak Load (gf/mil/in) | Elongation @ peak (%) | Tensile Strength (Mpa) | Percent set after 150% cycle (%) |
|---|---|---|---|---|---|
| Sample 1: 100% VISTAMAXX 6102 FL polyolefin-based elastic | MD | 933.6 | 1028.9 | 14.2 | 12.2 |

TABLE 1-continued

Physical properties of VISTAMAXX polyolefin-based elastic film and dispersed reinforcing elongated inclusion structure VISTAMAXX polyolefin-based elastic films

|  | | Peak Load (gf/mil/in) | Elongation @ peak (%) | Tensile Strength (Mpa) | Percent set after 150% cycle (%) |
|---|---|---|---|---|---|
| Sample 2: 92.5% VISTAMAXX polyolefin-based elastic, 7.5% LOTADER polyolefin-based epoxy resin | | 1152.6 | 946.8 | 17.5 | 13.1 |
| Sample 3: 90% VISTAMAXX polyolefin-based elastic, 5% LOTADER polyolefin-based epoxy resin, 5% PLA | | 1060.8 | 929.7 | 16.1 | 26 |
| Sample 1: 100% VISTAMAXX polyolefin-based elastic | CD | 844.92 | 1186.7 | 12.8 | 14.6 |
| Sample 2: 92.5% VISTAMAXX polyolefin-based elastic, 7.5% LOTADER polyolefin-based epoxy resin | | 1050.1 | 1241.7 | 16.0 | 14 |
| Sample 3: 90% VISTAMAXX polyolefin-based elastic, 5% LOTADER polyolefin-based epoxy resin, 5% PLA | | 1114.2 | 1293.3 | 17.0 | 14.4 |

Table 1 demonstrates the superior performance of Sample 3: 90% VISTAMAXX polyolefin-based elastic/5% Lotader/5% PLA blend in every specific property to 100% of VISTAMAXX polyolefin-based elastic film, especially in the CD. Sample 3 generated a higher permanent set of 26% in the MD due to the micro-domain inclusion of PLA, which is typical for a high-modulus polymer mixing with elastic polymer. However, a greater than 33% higher tensile strength was achieved in the CD without sacrificing elasticity as compared to pure VISTAMAXX polyolefin-based elastic film. Specifically, Sample 3 demonstrated 33% higher tensile strength as compared to Sample 1 with substantially similar percent set. There are no reports of such phenomena in other plastic/elastic blend systems. A similar behavior was observed for VISTAMAXX polyolefin-based elastic/LOTADER polyolefin-based epoxy resin blends (Sample 2). Without being limited to a specific theory, reduced MD elongation of the blend is possibly due to physical entanglement of the LOTADER polyolefin-based epoxy resin chains with the VISTAMAXX polyolefin-based elastic chain because no chemical reaction occurred between the two polymers. The higher MD strength and percent set is what is typically seen with elastomeric/plastic blends, but the CD characteristics demonstrated herein are not characteristic of typical blends.

SEM studies as illustrated in FIGS. 1-8 indicated a dispersed reinforcing elongated inclusion structure was created in the VISTAMAXX polyolefin-based elastic matrix through inclusion of PLA/LOTADER polyolefin-based epoxy resin micro-domains in the VISTAMAXX polyolefin-based elastic matrix. The structure and property relationship of dispersed reinforcing elongated inclusion structure VISTAMAXX polyolefin-based elastic blend demonstrated that the inclusion of PLA micro-domains in the VISTAMAXX polyolefin-based elastic matrix enhanced tensile strength and maintained elastic properties (elongation and percent set) in the CD as shown in the figures.

Figure 6:
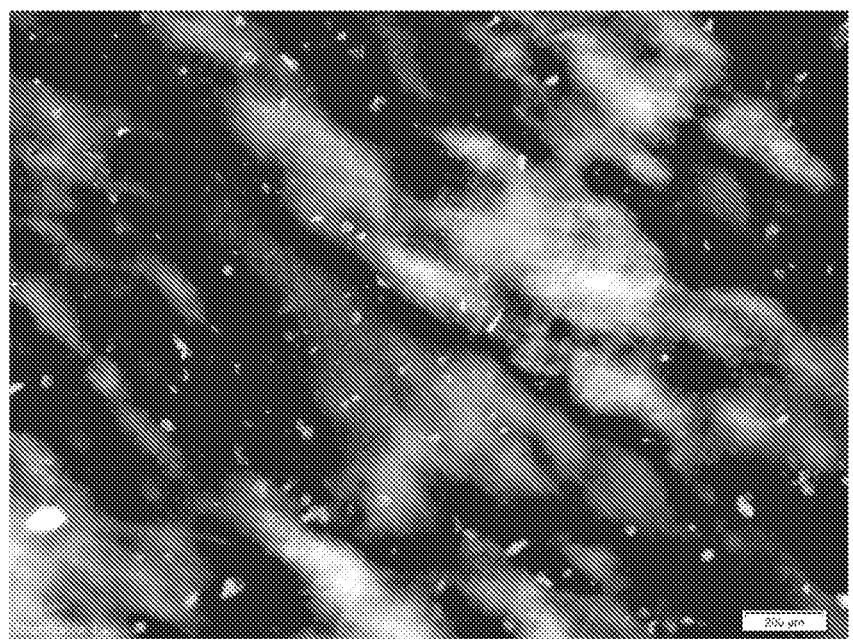
FIG. 6 is an SEM microphotograph of a surface of the film of 50% stretching in the CD, the micro-domains aggregated and shifting to near 45 degrees.
Figure 7:
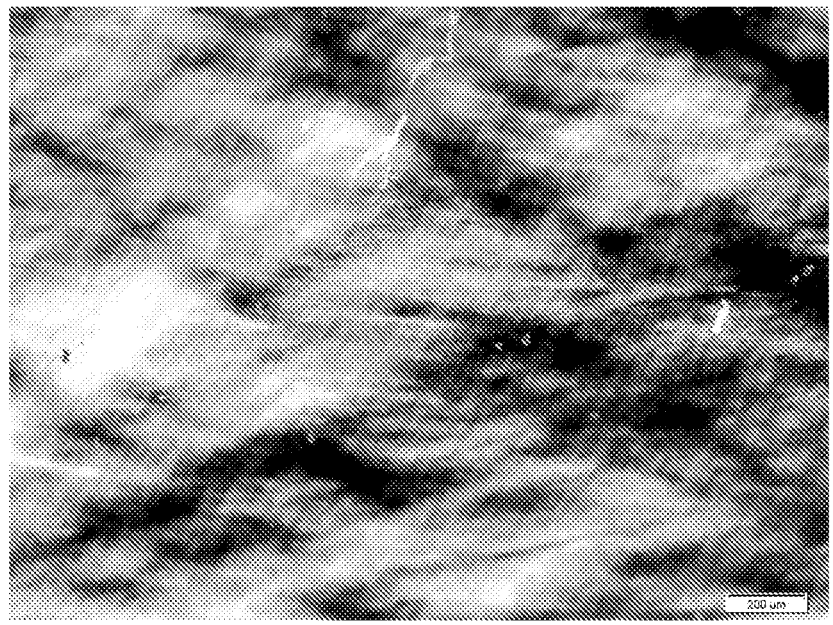
FIG. 7 is an SEM microphotograph of a surface of the film of 100% CD stretching.
Figure 8:
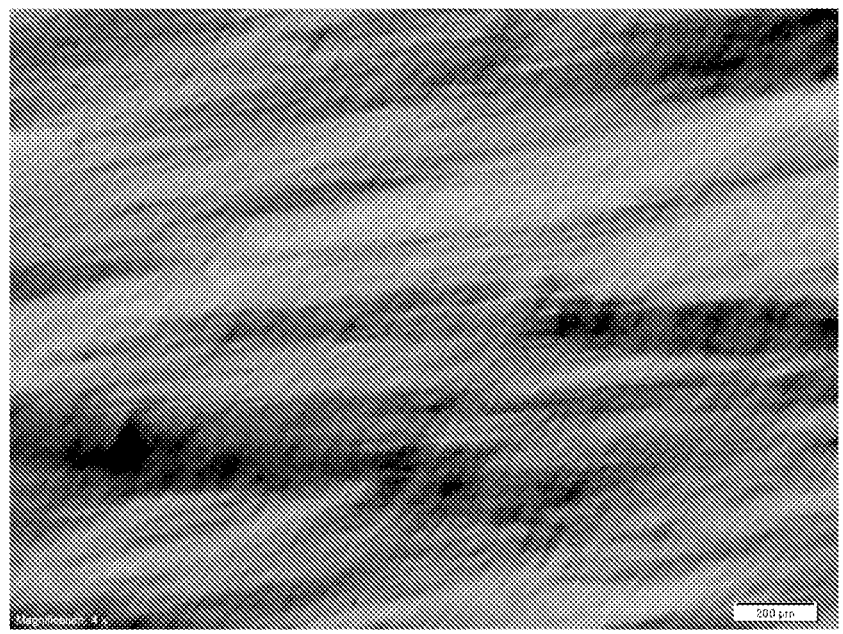
FIG. 8 is an SEM microphotograph of a surface the film of 200% CD stretching where the micro-domains most align with the CD.

A polarized optical microscope study found that dispersed reinforcing elongated inclusion structure micro-domains reversibly re-orient during CD stretching (see FIGS. 6-8). The micro-domains reversibly re-orient under CD stretching, providing reinforced elastic tensile strength without negatively impacting elastic properties in the CD. Specifically, the CD orientation during CD stretch provides the higher tensile strength (33% higher; 17.0 vs. 12.8) with virtually the same level of percent set as the control material (14.4 vs. 14.6). In addition, the peak elongation is also higher.

In a first particular aspect, a thermoplastic polyolefin elastomer film includes a continuous phase that includes a thermoplastic polyolefin elastomer and a nanoinclusion additive dispersed within the continuous phase in the form of discrete domains, wherein each discrete domain is elongated with a long axis, wherein the axes are aligned in the machine direction (MD) when the film is relaxed, and wherein the axes are aligned in the cross direction (CD) when the film is stretched in the CD.

A second particular aspect includes the first particular aspect, wherein the nanoinclusion additive includes a plurality of nanoinclusions having an average cross-sectional dimension of about 800 nanometers or less.

A third particular aspect includes the first and/or second aspects, wherein the polyolefinic elastomer is a polypropylene elastomer.

A fourth particular aspect includes one or more of aspects 1-3, wherein the nanoinclusion additive is a terpolymer of ethylene, acrylic ester, and glycidyl methacrylate.

A fifth particular aspect includes one or more of aspects 1-4, wherein the nanoinclusion additive constitutes from about 0.05 wt. % to about 20 wt. % of the film, based on the weight of the continuous phase.

A sixth particular aspect includes one or more of aspects 1-5, further comprising a microinclusion additive dispersed within the continuous phase in the form of discrete domains.

A seventh particular aspect includes one or more of aspects 1-6, wherein the microinclusion additive is a polymer.

An eighth particular aspect includes one or more of aspects 1-7, wherein the polymer of the microinclusion additive is a styrenic copolymer, functionalized polyolefin, or polyester.

A ninth particular aspect includes one or more of aspects 1-8, wherein the polymer of the microinclusion additive is polylactic acid.

A tenth particular aspect includes one or more of aspects 1-9, wherein the nanoinclusion additive is a polymer having a nonpolar component.

An eleventh particular aspect includes one or more of aspects 1-10, wherein the polymer is a microcrystalline polyolefin wax.

A twelfth particular aspect includes one or more of aspects 1-11, wherein the polymer further contains a polar component.

A thirteenth particular aspect includes one or more of aspects 1-12, wherein the polymer is a functionalized polyolefin.

A fourteenth particular aspect includes one or more of aspects 1-13, wherein the functionalized polyolefin is a polyepoxide.

A fifteenth particular aspect includes one or more of aspects 1-14, wherein the thermoplastic polyolefin elastomer film further comprises a compatibilizer.

A sixteenth particular aspect includes one or more of aspects 1-15, wherein the thermoplastic polyolefin elastomer film further comprises an interphase modifier.

In a seventeenth particular aspect, an article includes a polyolefinic elastomeric film including a continuous phase that includes a thermoplastic polyolefin elastomer and a nanoinclusion additive dispersed within the continuous phase in the form of discrete domains, wherein each discrete domain is elongated with a long axis, wherein the axes are aligned in the machine direction (MD) when the film is relaxed, and wherein the axes are aligned in the cross direction (CD) when the film is stretched in the CD.

An eighteenth particular aspect includes the seventeenth particular aspect, wherein the article is a laminate.

A nineteenth particular aspect includes the seventeenth and/or eighteenth aspects, wherein the article is a package.

A twentieth particular aspect one or more of aspects 17-19, wherein the article is an absorbent article.

While the disclosure has been described in detail with respect to the specific aspects thereof, it will be appreciated that those skilled in the art, upon attaining an understanding of the foregoing, can readily conceive of alterations to, variations of, and equivalents to these aspects. Accordingly, the scope of the present disclosure should be assessed as that of the appended claims and any equivalents thereto.

What is claimed is:

1. A thermoplastic polyolefin elastomer film comprising: a continuous phase that includes a thermoplastic polyolefin elastomer and a nanoinclusion additive dispersed within the continuous phase in the form of discrete domains, wherein each discrete domain is elongated with a long axis, wherein the axes are aligned in a machine direction (MD), and wherein the axes are aligned in a cross direction (CD) when the film is stretched in the CD and reversibly re-orient to return to be aligned in the MD when the film is relaxed.

2. The film of claim 1, wherein the nanoinclusion additive includes a plurality of nanoinclusions having an average cross-sectional dimension of about 800 nanometers or less.

3. The film of claim 1, wherein the polyolefinic elastomer is a polypropylene elastomer.

4. The film of claim 1, wherein the nanoinclusion additive is a terpolymer of ethylene, acrylic ester, and glycidyl methacrylate.

5. The film of claim 1, wherein the nanoinclusion additive constitutes from about 0.05 wt. % to about 20 wt. % of the film, based on the weight of the continuous phase.

6. The film of claim 1, further comprising a microinclusion additive dispersed within the continuous phase in the form of discrete domains.

7. The film of claim 6, wherein the microinclusion additive is a polymer.

8. The film of claim 7, wherein the polymer of the microinclusion additive is a styrenic copolymer, functionalized polyolefin, or polyester.

9. The film of claim 7, wherein the polymer of the microinclusion additive is polylactic acid.

10. The film of claim 1, wherein the nanoinclusion additive is a polymer having a nonpolar component.

11. The film of claim 10, wherein the polymer is a microcrystalline polyolefin wax.

12. The film of claim 10, wherein the polymer further contains a polar component.

13. The film of claim 10, wherein the polymer is a functionalized polyolefin.

14. The film of claim 13, wherein the functionalized polyolefin is a polyepoxide.

15. The film of claim 1, wherein the thermoplastic polyolefin elastomer film further comprises a compatibilizer.

16. The film of claim 1, wherein the thermoplastic polyolefin elastomer film further comprises an interphase modifier.

17. An article comprising a polyolefinic elastomeric film including a continuous phase that includes a thermoplastic polyolefin elastomer and a nanoinclusion additive dispersed within the continuous phase in the form of discrete domains, wherein each discrete domain is elongated with a long axis, wherein the axes are aligned in a machine direction (MD) when the film is relaxed, and wherein the axes are aligned in a cross direction (CD) when the film is stretched in the CD and reversibly re-orient to return to be aligned in the MD when the film is relaxed.

18. The article of claim 17, wherein the article is a laminate.

19. The article of claim 17, wherein the article is a package.

20. The article of claim 17, wherein the article is an absorbent article.

* * * * *